United States Patent [19]

Bennett, Jr. et al.

[11] Patent Number: 4,954,475

[45] Date of Patent: Sep. 4, 1990

[54] ZINC-CONTAINING ORTHO-ALKYLATION CATALYST PRECURSOR AND CATALYST, AND PROCESS OF USE IN ALKYLATION OF PHENOLS

[75] Inventors: James G. Bennett, Jr., Glenmont; Gregory R. Chambers, Delmar, both of N.Y.

[73] Assignee: General Electric Company, Selkirk, N.Y.

[21] Appl. No.: 126,555

[22] Filed: Nov. 30, 1987

Related U.S. Application Data

[63] Continuation of Ser. No. 640,080, Aug. 13, 1984, abandoned.

[51] Int. Cl.$^5$ ............................................. B01J 23/02
[52] U.S. Cl. ............................. 502/343; 502/340; 568/790; 568/794; 568/804
[58] Field of Search ............... 502/328, 329, 340, 343; 568/804, 790, 794

[56] References Cited

U.S. PATENT DOCUMENTS

| | | | |
|---|---|---|---|
| 2,092,870 | 9/1937 | Beamer | 568/403 |
| 2,193,464 | 3/1940 | Natta | 502/343 |
| 2,448,942 | 5/1944 | Winkler | 568/804 |
| 2,552,300 | 5/1951 | Timm et al. | 568/487 |
| 3,347,936 | 11/1955 | Froitzheim et al. | 502/340 |
| 3,446,856 | 5/1969 | Hamilton | 568/747 |
| 3,479,410 | 11/1969 | Hamilton, Jr. | 568/804 |
| 3,546,140 | 12/1970 | Gutmann et al. | 562/329 |
| 3,873,623 | 3/1975 | Kablaoui | 568/306 |
| 3,873,628 | 3/1975 | Van Sorge | 568/804 |
| 3,911,039 | 10/1975 | Grasselli | 502/328 X |
| 3,972,828 | 8/1976 | Van Sorge | 502/159 |
| 3,972,836 | 8/1976 | Van Sorge | 252/471 |
| 3,974,229 | 8/1976 | Van Sorge | 568/794 |
| 4,021,371 | 5/1977 | Petro | 502/328 X |
| 4,048,239 | 9/1977 | Smith | 568/804 |
| 4,150,063 | 4/1979 | Besozzi | 502/328 X |
| 4,475,001 | 10/1984 | Leston | 568/784 |

FOREIGN PATENT DOCUMENTS

0717588 10/1954 United Kingdom .

Primary Examiner—William R. Dixon, Jr.
Assistant Examiner—James M. Hunter, Jr.
Attorney, Agent, or Firm—Hedman, Gibson, Costigan & Hoare

[57] ABSTRACT

Catalyst precursor compositions comprising a mixture of magnesium oxide or a source of magnesium oxide and a water insoluble zinc compound are described. The compositions are calcinable to a catalyst that is useful in reactions for the ortho-alkylation of phenols.

16 Claims, No Drawings

ZINC-CONTAINING ORTHO-ALKYLATION CATALYST PRECURSOR AND CATALYST, AND PROCESS OF USE IN ALKYLATION OF PHENOLS

This is a continuation of application Ser. No. 640,080, filed Aug. 13, 1984, now abandoned.

BACKGROUND OF THE INVENTION

Processes for the ortho-alkylation of phenols are known in the art. In such a process, a phenolic compound or mixture of phenolic compounds having a replaceable hydrogen atom in at least one of the two ortho positions on the ring is reacted with an alkylation catalyst. By way of illustration, an excess of methanol is reacted with a mixture of phenol and ortho-cresol at elevated temperatures, using a catalyst, to produce 2,6-xylenol. This product is particularly useful as a monomer that can be polymerized to form poly(2,6-dimethyl-1,4-phenylene) ether, a high performance engineering thermoplastic material Various ortho-alkylation catalysts and methods for their preparation and use are described in the patent literature. A number of such catalysts have been disclosed by Van Sorge, including magnesium oxide (U.S. Pat. No. 3,972,828), finely divided mixtures of magnesium oxide and manganese oxide (U.S. Pat. No. 3,972,836 and U.S. Pat. No. 3,974,229), and mixtures of magnesium oxide and manganese sulfate (U.S. Pat. No. 3,873,623). The magnesium oxide in these catalysts may be derived by the thermal decomposition of magnesium carbonate.

Hamilton, U.S. Pat. No. 3,446,856 described a process for the vapor phase ortho-methylation of phenols in the presence of a magnesium oxide catalyst As taught in column 6, beginning on line 53, the catalyst can be used in conjunction with minor amounts of other metal compounds exerting a promoting action, such as zinc oxide, lead oxide and zinc chromite. As taught further in column 6, on lines 66–69, the promoter can be used as a heterogeneous mixture throughout the catalyst bed, be coprecipitated with the magnesium oxide, or be used as a separate zone at the reactor inlet end. If coprecipitated with the magnesium oxide, Hamilton's promoter must necessarily be an initially soluble compound, although not expressly indicated in the patent disclosure. The temperatures at which the catalyst is calcined, and thus activated, are relatively high, 475°–600° C. (column 7, lines 21–25).

SUMMARY OF THE INVENTION

This invention provides, in one aspect, a catalyst precursor composition comprising a mixture of
(a) a material selected from the group consisting of magnesium oxide and compounds that are thermally decomposable to magnesium oxide; and
(b) a substantially water insoluble zinc compound,
the precursor being calcinable, that is, heat activatable, to a catalytic composition useful in reactions for the ortho-alkylation of phenolic compounds.

Other facets of the invention comprise an active catalyst which is the calcined product derived by heating the above mentioned mixture, as well as the use of the catalyst in a process for the ortho-alkylation of a phenolic compound.

Special mention is made of the utility of the present catalyst in reactions for the ortho-methylation of phenol and of mixtures of phenol and ortho-cresol to produce ortho-cresol and 2,6-xylenol, respectively. The catalyst is especially efficacious for making ortho-cresol in good yield and favors production of this material over 2,6-xylenol from phenol. Ortho-cresol itself is useful as a preservative and disinfectant, as well as a starting material for the production of 2,6-xylenol.

DETAILED DESCRIPTION OF THE INVENTION

As indicated, the catalyst compositions of this invention are based on magnesium compounds and zinc compounds. Useful as the magnesium compound are magnesium oxide as well as magnesium compounds, such as salts, that are thermally decomposable to magnesium oxides at the temperatures of catalyst activation. Such decomposable compounds include magnesium carbonate, basic magnesium carbonate and magnesium hydroxide.

The term "basic magnesium carbonate" is employed in this disclosure to refer to materials represented by the formula

$$xMgCO_3 \cdot Mg(OH)_2 \cdot xH_2O$$

in which each x is independently a number average from about 3 to about 5.

Especially preferred for use in this invention is basic magnesium carbonate, usually in finely divided particulate form.

The zinc moiety of the catalyst is provided, as indicated, by a substantially water insoluble zinc compound. By "substantially water insoluble" is meant that no more than about 0.001 gram of the compound dissolves in 100 cubic centimeters of cold water. Examples of suitable zinc compounds for use in this invention include zinc oxide, zinc phosphate, zinc stearate, zinc sulfide, zinc carbonate, zinc hydroxide, zinc oxalate and zinc silicate. Zinc oxide is especially preferred.

Preparation of the catalyst composition is readily accomplished by use of either dry or wet techniques. In one procedure, dry powders of the compounds are blended in a mechanical mixer or on a roll mill. In another procedure, a slurry of the compounds in water is formed, agitated to achieve a uniform dispersion and the solids are then centrifuged, recovered and dried.

Preferably, though not necessarily, a minor amount of a thermally decomposable polymer, for instance, a polyphenylene oxide, is included in the catalyst mixture to facilitate the formation of pores in the catalyst composition during the subsequent calcining treatment. Poly(2,6-dimethyl-1,4-phenylene)ether reisn is especially favored for this purpose. Amounts of the polymer of from about 0.1 to about 20 percent by weight, based on the total catalyst weight, are typical for use in this invention.

Similarly, a shaping aid for the catalyst components may be employed, if desired. This may be selected from conventional materials commonly used for such purposes. Powdered graphite is preferred, in amounts from about 1 to about 5% by weight, again based on the total weight of the catalyst.

The mixture of magnesium and zinc compounds as well as any polymers and/or shaping aids that may be present, once formed, is then shaped into a desired physical form, for instance, into tablets, pellets, or cylinders, using standard shaping techniques and equipment.

After shaping, the mixture, which at this stage is in a pre-activated state, is treated for activation by calcining at a suitably elevated temperature. Notably, in accordance with the present invention relatively low calcining temperatures are sufficient to achieve a highly active catalyst, using the present materials. Thus, calcining temperatures from about 350° to 500° C. are typical, in contrast to many prior art calcining procedures where temperatures of 500° C., and higher, are the norm. Calcining periods of up to 24 hours are employed to obtain the present catalyst. The calcining treatment itself may be carried out in out in various ways. The treatment can be applied to the precursor mixture in situ in an ortho-alkylation reactor, or outside the reactor prior to loading. The calcining may be conducted in various environments, such as air, relatively pure oxygen, in inert gases such as nitrogen or argon, in a vacuum, or even in the presence of a feed mixture of the co-reactants to be catalyzed. Heat may be applied directly to the precursor particles, as in an oven or by contacting with the heated walls of the reactor chamber, or through convection, as by contacting with a preheated stream of gas such as air, nitrogen, etc.

As the mixture is being calcined, small pores develop in the composite, thereby exposing more surface area, which is beneficial to the activity of the catalyst and may prolong the useful life. A surface area of at least 25 square meters per gram of catalyst weight is desired, and from 25 to 450 square meters per gram is especially preferred. Such surface areas will normally be achieved using the conditions described.

Desirably, the final catalyst will contain from about 0.25 to about 20 percent by weight of zinc oxide and, correspondingly, from about 99.75 to about 80 percent by weight of magnesium oxide.

The catalyst is useful in a process according to the invention in which a phenolic compound is substituted in the ortho position or positions with an alkyl group or groups, using vapor phase conditions of temperature. Useful as the phenolic starting material are compounds having the formula

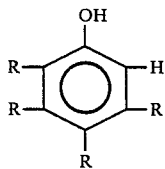

in which each R is independently a monovalent substituent selected from the group consisting of hydrogen, alkyl, preferably $C_1$ to $C_{12}$ alkyl, phenyl and alkyl substituted phenyl.

As co-reactant for the phenolic compound in the process, branched or linear alkyl alcohols having up to 16 carbon atoms are preferred. Examples include methyl, ethyl, propyl, isopropyl, butyl, isobutyl, tert-butyl, amyl, isoamyl, hexyl, heptyl, octyl, nonyl, decyl, lauryl, cetyl and cyclohexyl alcohol. Especially preferred are alkyl alcohols of up to 6 carbon atoms, the most preferred of which is methanol The reaction mixture may also contain up to about 40 percent by weight of water.

Illustratively, a reaction feed mixture of the phenolic compound or compounds, the alkyl alcohol and water is vaporized, then passed through a reactor heated to a temperature of at least 300° C., preferably from 350° to 500° C., containing the described catalyst Notably, the present reaction temperatures are lower than those taught in Hamilton, U.S. Pat. No. 3,446,856, which prescribes the temperature range 475° to 600° C. for ortho-alkylation.

As is customary, at least one mole of alkyl alcohol, and more usually from one to three moles, for each ortho position on the phenol to be alkylated should be employed. Thus, for instance, if phenol, which has two ortho hydrogens per molecule is to be mono-methylated to produce ortho-cresol, it is recommended to use from two to six moles of methanol per mole of phenol Larger yields will be obtained using the higher ratios of methanol to phenol within this range.

The ortho-alkylation reaction can be conducted with use of various conditions of temperature, pressure, flow rate of reactants, vapor space velocity of reactants over catalyst, length of catalyst feed, and so forth. In general, ambient conditions of pressure are sufficient, although superatmospheric or subatmospheric pressures are possible, if desired The vapors emitting from the reactor are collected, condensed and separated into individual constituents by conventional procedures, e.g., crystallization or distillation.

The invention is further illustrated in the examples, which are intended only to show specific, not limiting, embodiments. In these examples, the ortho-alkylation reactor used was as follows:

THE REACTOR

The Reactor is comprised of two stainless steel tubes, both of which are oriented along a vertical axis, one of which has a length of 15 inches (38.1 centimeters), the other of which has a length of 24 inches (60.96 centimeters). Each tube has an inner diameter of ¾ inch (1.91 centimeters). The first tube functions as a vaporizer chamber. The second tube, filled to a depth of two inches along the vertical with glass beads as a support for the catalyst, functions as a reactor chamber. Both tubes are partially immersed in a fused salt bath, the first (vaporizer) to a depth of 8 inches (20.3 centimeters), the second (reactor) to a depth of 17 inches (42.3 centimeters). The two tubes are physically joined by means of a third tube, consisting of a two-inch long (5.1 centimeters) steel pipe, connected at one end to an opening in the first (vaporizer) tube 5 inches (12.7 centimeters) from its bottom end, and connected at the other end to an opening in the second (reactor) tube 14 inches (35.6 centimeters) from its bottom end. The connector pipe is fully immersed in the fused salt bath.

In practice, a feed stream of the co-reactants is sent from a reservoir through a metering pump into the vaporizer tube, where the feed is heated to a temperature sufficient to volatilize the constituents. The vapors from the vaporizer tube are passed through the connecting pipe, which serves as a preheater to bring the vapors up to the temperature of the reactor tube. Once in the reactor tube, the vaporized feed passes through the catalyst bed, where reaction takes place. Product vapors leave the bottom end of the reactor tube through a stainless steel outlet tube, having an inner diameter of ⅜ inch (0.95 centimeters), and are led to a water cooled condenser-receiver assembly where they are liquefied and recovered. The non-condensibles are scrubbed with water and measured by the use of a wet test meter.

PREPARATION OF CATALYSTS CONTAINING BOTH MAGNESIUM AND ZINC (THIS INVENTION)

Three hundred grams of commercial grade basic magnesium carbonate (Merck's DMQ-006) were slurried in 2000 milliliters of distilled water. Zinc oxide was added to equal portions of the magnesium carbonate slurry in varying amounts sufficient to make the following mixtures (with the contents indicated as a weight ratio):

| Sample No. | MgCO$_3$ ZnO |
|---|---|
| 1 | 90:10 |
| 2 | 90:5 |
| 3 | 90:1 |

Each of the mixtures was stirred for one hour and then filtered on a 3000-milliliter medium fritted filter. The resulting filter cakes were dried in a vacuum oven at 105° C. overnight, sieved through a 25 mesh screen, and blended with powdered graphite to make a mixture of 99.5:0.5 catalyst:graphite. In each case, the catalyst:graphite mixture was precompressed into semi-hard tablets, ground with mortar and pestle, sieved through a 25 mesh screen, and then re-tabletted to form tablets having the dimensions ⅛ inch by 3/16 inch and a hardness from 7 to 10 kp as measured on a Schleuniger hardness tester.

semi-hard tablets, ground with a mortar and pestle, sieved through a 25 mesh screen and retabletted to form ⅛ inch by 3/16 inch tablets (hardness between 7 and 10 kp on Schleuniger tester).

EXAMPLE

Each of the three catalysts in accordance with the invention, Samples 1,2 and 3 above, was evaluated in an ortho-alkylation process. In each case, the reactor was charged by filling the reactor tube to a depth of 12 inches with 110 milliliters of the catalyst, capping and placing it in a 370° C. fused salt bath, after which a stream of gaseous nitrogen was commenced over the catalyst bed at a rate of 2.0 standard cubic feet per hour (SCFH). The feed stream to the reactor consisted of 4/1 methanol/phenol and 20% water. The feed rate was 215 ml/hr., equivalent to a liquid having a space velocity (LHSV) of 1.95 hr.$^{-1}$, defining the volume of liquid per volume of catalyst per hour. This rate was maintained for the duration of the run, 502 hours. The pressure was 25 psi.

During the course of the run for each catalyst, a temperature program was followed in which the feed was established at 370° C., and then the temperature was raised to 440° C. (reached in about 1½ to 2½ hours) and maintained there for the balance of the run.

For purposes of comparison, an identical run was also made using the control catalyst described above. The results for each catalyst are reported in Tables 1 and 2.

TABLE 1

SUMMARY OF ACTIVITY VS. TIME

| Catalyst | Time, hrs. | Off Gas, SCFH | Phenol, Wt. % | o-Cresol, Wt. % | 2,6-Dimethylphenol Wt. % | 2,4,6-Trimethylphenol, Wt. % |
|---|---|---|---|---|---|---|
| Control | 151 | 0.420 | 1.44 | 13.56 | 79.63 | 7.30 |
| ZnO 1% | | 0.350 | 19.39 | 53.83 | 24.10 | 1.29 |
| ZnO 5% | | 0.610 | 21.41 | 51.69 | 24.23 | 1.38 |
| ZnO 10% | | 0.640 | 20.20 | 49.18 | 27.62 | 1.70 |
| Control | 311 | 0.360 | 3.93 | 18.12 | 71.74 | 5.40 |
| ZnO 1% | | 0.200 | 29.22 | 53.94 | 15.20 | 0.54 |
| ZnO 5% | | 0.540 | 26.52 | 52.50 | 19.17 | 0.70 |
| ZnO 10% | | 0.620 | 28.86 | 51.56 | 17.72 | 0.72 |
| Control | 414 | 0.280 | 6.31 | 21.09 | 66.01 | 5.24 |
| ZnO 1% | | 0.120 | 41.37 | 50.82 | 6.31 | 0.35 |
| ZnO 5% | | 0.390 | 36.13 | 54.31 | 7.88 | 0.40 |
| ZnO 10% | | 0.470 | 36.37 | 53.37 | 8.56 | 0.44 |

TABLE 2

SUMMARY OF TIME WEIGHTED AVERAGES AFTER 414 HOURS

| Catalyst | Temp., °F. | Off Gas, SCFH | Phenol, Wt. % | o-Cresol Wt. % | 2,6-Dimethylphenol, Wt. % | p-Cresol, Wt. % | Methylethylphenol, Wt. % | 2,4-Dimethylphenol, Wt % | 2,4,6-Trimethylphenol, Wt % |
|---|---|---|---|---|---|---|---|---|---|
| Control | 440 | 0.331 | 4.86 | 18.60 | 68.09 | 0.14 | 0.19 | 0.79 | 6.81 |
| ZnO 1% | 440 | 0.370 | 24.36 | 47.64 | 24.33 | 0.11 | 0.20 | 0.97 | 2.37 |
| ZnO 5% | 440 | 0.664 | 23.33 | 47.61 | 25.48 | 0.09 | 0.22 | 1.00 | 2.23 |
| ZnO 10% | 440 | 0.776 | 24.26 | 47.12 | 24.96 | 0.08 | 0.24 | 1.05 | 2.24 |

PREPARATION OF CONTROL CATALYST (TO BE USED FOR COMPARISON)

Six hundred grams of commercial grade basic magnesium carbonate (Merck's DMQ-006) were slurried in 4000 milliliters of distilled water. The magnesium carbonate slurry was stirred for one hour, then filtered on a 3000-milliliter capacity medium fritted filter. The filter cake was dried in a vacuum oven at 105° C. overnight, sieved through a 25 mesh screen and blended with powdered graphite to make a 99.5:0.5 catalyst:graphite mixture. The mixture was precompressed into As can be seen from the Tables, the zinc oxide-containing catalysts in accordance with the invention are effective to promote ortho-alkylation, with production of o-cresol being favored over time. After about 150 hours, the 50% conversion mark to ortho-cresol was reached for all three of the zinc oxide-containing catalysts, and this remained stable throughout the rest of the run in each case. The performances of the three zinc oxide-containing catalysts were virtually the same in all aspects except for off-gas production, with the amount of off gas increasing as the percent of zinc oxide in the catalyst was increased.

Other modifications and variations of this invention are possible in view of the description thus provided. It should be understood, therefore, that changes may be made in the particular embodiments shown which are within the scope of the invention defined in the appended claims.

We claim:

1. An active ortho-alkylation catalyst composition which, in an alkylation reaction conducted at a temperature between 300° C. and 440° C., yields phenols selected from the group consisting of 2-alkylphenols and 2,6-dialkylphenols in excess of phenols alkylated in the para position, comprising a mixture of
   (a) a material selected from the group consisting of magnesium oxide and compounds that are thermally decomposable to magnesium oxide; and
   (b) up to about 20% by weight of a substantially water insoluble zinc compound, said composition having been calcined to an active ortho-alkylation catalyst by heating at a temperature from about 350° to 440° C.

2. A composition according to claim 1, in which component (a) comprises one or more magnesium compounds selected from the group consisting of magnesium carbonate, basic magnesium carbonate, magnesium hydroxide, and magnesium oxide.

3. A composition according to claim 1, in which component (a) is magnesium carbonate.

4. A composition according to claim 1, in which component (a) is basic magnesium carbonate.

5. A composition according to claim 1, in which component (a) is magnesium hydroxide.

6. A composition according to claim 1, in which component (a) is magnesium oxide.

7. A composition according to claim 1, in which component (b) is zinc oxide.

8. A composition according to claim 1, in which the mixture has been formed by dry blending components (a) and (b).

9. A composition according to claim 1, in which the mixture has been formed by slurrying (a) and (b) in an aqueous medium.

10. A composition according to claim 1, which also includes an amount of a polymeric additive prior to calcining.

11. A composition according to claim 10, in which the polymer is a polyphenylene ether resin.

12. A composition according to claim 10, in which the polymer is poly(2,6-dimethyl-1,4-phenylene)ether.

13. A composition according to claim 1, which has been shaped.

14. A catalyst according to claim 1, having a surface area of at least 25 square meters per gram.

15. A catalyst according to claim 1, having a surface area of 25 to 450 square meters per gram.

16. An active ortho-alkylation catalyst composition which, in an alkylation reaction conducted at a temperature between 300° C. and 440° C., yields phenols selected from the group consisting of 2-alkylphenols and 2,6-dialkylphenols in excess of phenols alkylated in the para position, consisting essentially of a mixture of
   (a) a material selected from the group consisting of magnesium oxide and compounds that are thermally decomposable to magnesium oxide; and
   (b) up to about 20% by weight of a substantially water insoluble zinc compound, said composition having been calcined to an active ortho-alkylation catalyst by heating at a temperature from about 350° to 440° C.

* * * * *